United States Patent [19]

Chipens et al.

[11] 4,285,857
[45] Aug. 25, 1981

[54] CYCLIC ANALOGUES OF CALLIDINE

[76] Inventors: Gunar I. Chipens, ulitsa Apes, 12, kv. 81; Felix K. Mutulis, ulitsa Bikernieku, 77, kv. 52; Olga E. Lando, ulitsa Berzupes, 31a, kv. 21; Natalia V. Myshlyakova, ulitsa Gorkogo, 33, kv. 18, all of Riga, U.S.S.R.

[21] Appl. No.: 78,950

[22] Filed: Sep. 26, 1979

[30] Foreign Application Priority Data

Sep. 29, 1978 [SU] U.S.S.R. ................................ 2699155

[51] Int. Cl.³ .............................................. C07C 103/52
[52] U.S. Cl. ................................................ 260/112.5 R
[58] Field of Search ................................... 260/112.5 R

[56] References Cited

U.S. PATENT DOCUMENTS 3,216,992  11/1965  Bodansky et al. ............. 260/112.5 R
3,247,181  4/1966  Schwyzer et al. ............. 260/112.5 R

OTHER PUBLICATIONS

J. Meienhofer., Liebigs Ann. Chem. Bd. 691, (1965), pp. 218–225.

Primary Examiner—Delbert R. Phillips
Attorney, Agent, or Firm—Steinberg & Raskin

[57] ABSTRACT

Novel cyclic analogues of callidine have the following general formula:

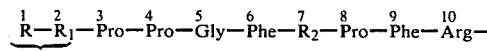

wherein Pro is moiety of L-proline, Gly—that of glycine, Phe—phenylalanine, Arg—L-argenine; R is a residue of $\alpha$- or $\omega$-aminoacid or peptide; $R_1$ is a residue of $\alpha$- or $\omega$- amino-acid; $R_2$ is L-serine or glycine, the carbonyl group of arginine being connected either with R or with $R_1$ by means of a covalent peptide bond using the $\omega$-amino group of the aminoacid located in the 1 or 2 position of the calladine sequence. The novel compounds according to the present invention possess a prolonged hypotensive effect of selective character.

5 Claims, No Drawings

CYCLIC ANALOGUES OF CALLIDINE

FIELD OF THE INVENTION

The present invention relates to biochemistry and, more specifically, it relates the novel cyclic analogues of callidine.

The new compounds according to the present invention possess biological activity and are useful in medicine as an active principle of medicated compounds ensuring a prolonged hypotensive effect.

Callidin pertains to pachykinins, i.e. compounds of the peptide nature which are formed in blood of animals and human beings and act as bioregulators in cardiovascular and other systems of the organism. A whole series of different pathological states and diseases of the organism are associated with disturbed anabolism and metabolism of pachykinins, as a consequence of which a great interest exists in the possible application thereof as medicaments. However, the principal disadvantage of the pachykinins and their analogues resides in a short-time action (the period of half-decay of callidine in the organism is 0.32 min), as well as a wide range of biological effects, i.e. absence of selectivity.

BACKGROUND OF THE INVENTION

In the literature there has been described only one cyclic analogue of callidine, namely cyclo-/(7-glycine)-callidine/, wherein for the formation of the cycle, in contrast to the compounds of the present invention, use is made of the α-amino group of lysine, not the ω-amino group. No biological activity has been found for this compound. (cf. J.lieb.Ann.Chem., 691, (1966), 218–224).

The compounds according to the present invention, i.e. cyclic analogues of callidine are novel and hitherto unknown in the literature.

BRIEF SUMMARY OF THE INVENTION

It is an object of the present invention to provide novel cyclic analogues of callidine which have a selective hypotensive effect.

This object is accomplished by the cyclic analogues of callidine according to the present invention which have the following general formula:

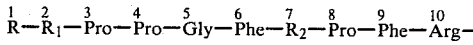

wherein Pro means a moiety of L-proline, Gly—that of glycine, Phe—moiety of L-phenylalanine, Arg—that of L-arginine; R is a residue of α- or ω-aminoacid or peptide; $R_1$ is a residue of α- or ω-aminoacid; $R_2$ is L-serine or glycine, carbonyl group of arginine being connected either with R or with $R_1$ by means of a covalent peptide bond using the ω-amino group of the aminoacid located in the 1 or 2 position of the callidine sequence. Numeration is given in accordance with the sequence of aminoacids in the callidine molecule.

Said compounds possess a prolonged hypotensive effect. The most active are the following compounds:

1. Cyclo-/$N^\epsilon$-callidine/ of the formula:

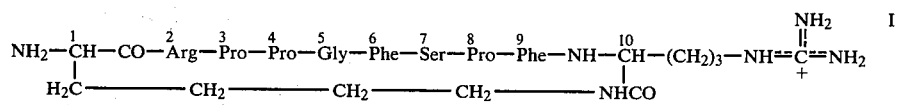

In a molecule of cyclo-/$N^\epsilon$-callidine/(I) there are covalently bonded the first and tenth aminoacids of callidine. For the formation of a cycle as the bridge structure use is made of a side chain of N-terminal aminoacid of callidinelysine, while the covalent (amide) bond is formed between the ε-amino group of the N-terminal lysine and the carbonyl group of the C-terminal aminoacid. As a result, a cyclic structure is formed containing 34 atomic groupings.

2. $N^\epsilon$-arginyl-cyclo/($N^\epsilon$-1-lysine, 6-glycine)-bradikinin/ of the formula:

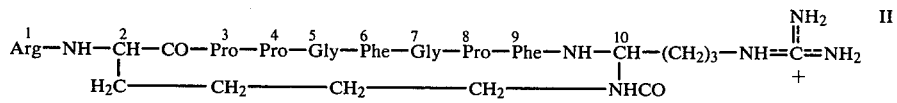

In a molecule of N-arginyl-α-cyclo-/($N^\epsilon$-1-lysine, 6-glycine)-bradikinin/(2) lysine and arginine of naturally-occurring callidine are interpositioned as to their sites of location and the cycle is closed between lysine in the position 2 and arginine in the position 10. Arginine in the position 1 is outside the cycle. The position 7 of naturally-occurring callidine is modified, i.e. glycine moiety is introduced instead of serine moiety. Just as in the compound (I) the carbonyl group of the C-terminal arginine is connected with the ε-amino group of lysine with the formation of a peptide bond. As a result, a cyclic structure is formed including 31 atomic groupings.

3. Cyclo/(ω-aminodecanoyl)bradikinin/ having the formula:

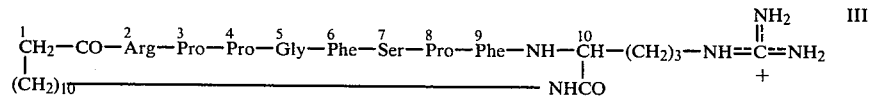

This compound (III) is an analogue of callidine, wherein the first aminoacid (lysine) is substituted with ω-aminocarboxylic acid having an extended chain of methylene groups, namely ω-aminododecane acid (11 methylene groups), while the ω-amino group of the terminal moiety of the analogue is connected with the C-terminal carbonyl group of the molecule, i.e. arginine moiety, thus forming a cyclic system including 40 atomic groupings. This compound may be also regarded as an analogue of callidine, wherein the N-terminal lysine is substituted with ω-aminododecane acid, or as an analogue of bradikinin, wherein ω-aminododecane acid is attached to the N-terminal.

4. Cyclo-/(ω-aminododecanoyl-ω-aminododecanoyl) bradikinin/of the formula:

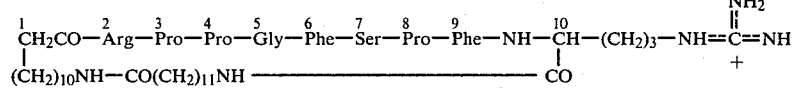 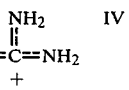   IV

The compound (IV) is an analogue of callidine, wherein the first aminoacid (lysine) is substituted with dipeptide-ωaminododecanoyl-ω-aminododecane acid, with its amino group being connected with the carbonyl group of the C-terminal arginine thus forming a cyclic structure including 53 atomic groupings. Said cyclic structures are formed by the connection of the terminal aminoacid moieties of callidine sequetion by means of a covalent bond through bridging structures. The cycle size may be adjusted by varying the length of the bridging structure of aminoacids constituting the kinin molecule.

DETAILED DESCRIPTION OF THE INVENTION

The compounds according to the present invention specified hereinabove are white powders which are soluble in water and alcohols.

Pharmacological activity of these compounds has been studied experimentally on animals.

The tests of the effect of compounds (I) and (II) on arterial pressure of urethane-narcotized rats upon intravenous injection have shown that compounds (I) and (II), in contrast to bradikinin, possess a clearly pronounced prolonged depressive effect. The threshold dose of brakinidin is 0.5 mcg/kg, while that of compounds (I) and (II) is 5 mcg/kg. In a dose of 50 mcg/kg compounds (I) and (II) cause equidepressive, though considerably longer effect, as compared to that of bradikinin, which effect is not different in its duration for compounds (I) and (II). This drop of arterial pressure by 30–40 mm Hg under the effect of compounds (I) and (II) lasts for 5–7 minutes, followed by a 2-hour regain of 80% of the starting level of arterial pressure. The duration of bradikinin effect is only 30 seconds. Increasing doses of compounds (I) and (II) up to 250 mcg/kg results in a sharp drop of arterial pressure and death of the test animals.

In the in vitro experiments on an isolated rat uterus it has been found that compound (II), in a concentration within the range of from $10^{-10}$ to $10^{-6}$ mol/l, has no myotropic effect inherent in naturally-occurring bradikinin. In contrast to compound (II), compound (I) has a myotropic activity reaching 100% of that of bradikinin, but revealed at a concentration by two orders of magnitude higher than that of bradikinin.

The tests of the effect of compound (III) on arterial pressure of urethane-narcotized rats upon intravenous administration have shown that, unlike bradikinin, compound (III) has a prolonged depressive effect. The threshold dose of bradikinin is 0.5 mcg/kg; that of compound (III) is 50 mcg/kg. In a dose within the range of from 50 mcg/kg to 250 mcg/kg there is observed the relationship of the effect vs, dose of compound (III). Equidepressive effects (30–40 mm Hg) are developed at doses of 50 and 250 mcg/kg for bradikinin and compound (III) respectively and last for 30 seconds for bradikinin and 35 minutes for compound (III), respectively, until restoration of the 100% starting level of arterial pressure. In similar experiments on dogs in doses of 5 and 100 mcg/kg, compound (I) causes a hypotensive effect by 20–25 mm Hg and arterial pressure regains its initial level after 10 minutes.

In the in vitro experiments on an isolated rat uterus it has been found that compound (III) possesses a myotropic activity constituting 81±7% of the activity of bradikinin taken as 100%, though manifesting in concentrations by three orders of magnitude higher than that of bradikinin. On the basis of the tests performed it has been found that cyclic analogues of callidine have a prolonged hypotensive effect of a selective character.

The synthesis of the above-mentioned cyclic analogues of callidine is carried out using conventional techniques of peptide chemistry.

Tert. butoxycarbonyl or benzyloxycarbonyl derivatives of aminoacids or peptides activated by the formation of pentafluorphenyl esters, p-nitrophenyl esters or azides, or mixed anhydrides are reacted with derivatives of aminoacids or peptides with a free amino group with a subsequent cleavage of the protective groups.

In doing so, the guanidine fraction of arginine is blocked by means of a nitro group or benzyloxycarbonyl group; hydroxy function of serine is blocked with benzyl ether. Then cyclization of the resulting peptide is effected through the stage of the formation of its pentafluorophenyl ester or N-hydroxysuccinimide ester, followed by a catalytic hydrogenation and isolation of the desired product. For a better understanding of the present invention some specific examples illustrating preparation of said cyclic analogues of callidine are given hereinbelow. Individuality of the resulting compounds has been identified using thin-layer chromatography techniques on plates "Silufol" or "Merck", Chromatographic mobilities $R_f$ are given for "Silufol" plates UV-254 in the following systems:

A—chloroform-ethanol-ethylacetate-acetic acid-water (85:5:8:2:0.25);
B—chloroform-ethanol-n.butanol-ethylacetate-water (10:6:4:3:1);
C—chloroform-methanol-water (40:30:5);
D—butanol-acetic acid-water (4:1:1);
E—ethylacetate-pyridine-acetic acid-water (5:5:1:3),
as well as electrophoretic mobility in respect of histidine on paper FN-16 in a 1 N or 5 N acetic acid. Stains of the compounds have been detected by visualization of the chromatograms in UV-light, as well as by spraying with ninhydrin or by means of chloro-reagent of benzidine. For all the compounds the data of elemental analysis were satisfactorily consistent with the calculated content of C, H, N. For identification of compounds use was also made of PMR spectra. Chemical displacements, shape and intensity of the obtained signals corresponded to the structure of peptides. The structure of the compounds was also supported by aminoacid analysis performed in a sealed ampule at the temperature of 100° C. for 24 hours.

Chromatographic purification of the compounds, unless otherwise specified, was effected on a modified instrument "Jobin-Ivon Chromatospac Prep. 100" using silica gel H 60 produced by "Merck" company.

EXAMPLE 1

7.17 g (15 mmol) of prolylphenylalanine p-nitrobenzyl ester hydrobromide and 6.61 g (16.5 mol) of pentafluorophenyl ester of tert.butoxycarbonyl-o-benzylserine are dissolved in 50 ml of dimethylformamide. N-Methylformalin is added to pH=8 (as described by placing a drop on a wet indicator paper). The solution is maintained for 30 minutes at room temperature, evaporated, the residue is dissolved in 50 ml of ethylacetate, washed with 50 ml of a 10% solution of potassium bisulphate, then with 50 ml of water, dried over anhydrous magnesium sulphate, filtered and evaporated to 15 ml, added with 100 ml of hexane and maintained at the temperature of 0° C. An oily product is precipitated which is dried at the temperature of 50° C. under 1 mm Hg pressure. The yield of p-nitrobenzyl ester of tert.butoxycarbonyl-o-benzylseryl-prolylphenylalanine (compound I) is 10.0 g (99%); $R_f$=0.55 (ethylacetate); 0.90 (A).

9.5 g of compound (I)/14 mmol/are dissolved in 50 ml of trifluoroacetic acid, kept for 20 minutes at room temperature, evaporated at 20° C. and the residue is rubbed with 100 ml of anhydrous ether. The resulting precipitate is filtered off, washed with ether and maintained over potassium hydroxide at 1 mm Hg. The yield of trifluoroacetate of p-nitrobenzyl ester of o-benzylserylpropylphenylalanine (compound 2) is equal to 8.04 g (94%). $\alpha_D^{20}$=−25.3° (c=1, dimethylformamide); $E_{his}$=0.60 (5 N acetic acid); $R_f$=0.06 (A); 0.46 (B); 0.76 (C); 0.58 (D).

6.89 g (10 mmol) of compound 2 and 4.7 g (11 mmol) of pentafluorophenyl ester of tert.butoxycarbonylphenylalanine are dissolved in 50 ml of dimethylformamide, added with N-methylmorpholine to pH=8, kept for 1 hour at room temperature and then evaporated; the residue is added with 50 ml of a 10% aqueous solution of potassium bisulphate and 20 ml of ether. The resulting precipitate is filtered-off, washed with water and then with ether; the product is dried over phosphorus pentoxide at 1 mm Hg. The yield of p-nitrobenzyl ester of tert.butoxycarbonylphenylalanyl-O-benzylserylprolylphenylalanine (compound 3) is 7.19 g (87.5%). $\alpha_D^{20}$=−32.5° (c=1, dimethylformamide). $R_f$=0.42 (A), 0.92 (B), 0.93 (C), 0.86 (D) 0.80 (E).

4.11 g (5.0 mmol) of compound 3 and 5 ml of hydrazinhydrate in 100 ml of methanol are stirred for three hours at room temperature, then kept for 20 hours at room temperature, evaporated to 20 ml, added with 100 ml of water and 50 ml of ether. The mixture is filtered, the filter cake is washed with water and then with ether. The yield of tert.butoxycarbonylphenylalanyl-o-benzylserylprolylphenylalanine hydrazide (compound 4) is 3.33 g (95%). $\alpha_D^{20}$=−51.2° (c=1, dimethylformamide). $R_f$=0.30 (A), 0.81 (B), 0.90 (C), 0.73 (D). To a solution of 12.8 g (34.3 mmol) of tert.butoxycarbonylnitroarginine and 3.80 ml (34.3 mmol) of N-methylmorpholine in 100 ml of dimethylformamide at the temperature of −15° C. there are added 4.63 ml (34.3 mmol) of chlorocarbonic acid isobutyl ester and then 10.0 g (22.8 mmol) of a powder of p-nitrophenyl ester of benzyloxycarbonyllysine hydrochloride are added thereto. The mixture is stirred for 30 minutes at a temperature of −10° C., then for 2 hours a solution of 2.55 ml (22.8 mmol) of N-methylmorpholine in 50 ml of dimethylformamide is dropwise added. Stirring is continued for an additional 30 minutes at a temperature of −20° C., then added with 1.33 ml (12.1 mmol) of β-dimethylaminoethylamine. Again the mixture is stirred for 30 minutes, evaporated and the residue is dissolved in a mixture of 100 ml of ethylacetate and 100 ml of water. The ethylacetate layer is washed with 10% solutions of potassium bicarbonate and potassium bisulphate (twice) and water; dried over magnesium sulphate, filtered and the filtrate is evaporated. The yield of p-nitrophenyl ester of α-benzyloxycarbonyl, ε-/tert.butoxycarbonylnitroarginyl/lisine (Compound 5) is equal to 13.5 g (86.5%); $\alpha_D^{20}$=−20.9° (c=1, dimethylformamide). $R_f$=0.80 (A), 0.90 (D).

20 g (53.6 mmol) of tert.butoxycarbonylnitroarginine and 3 ml of tetrahydrofuran are dispersed in 300 ml of anhydrous ethylacetate and under cooling (0° C.) added with 10.3 g (56 mmol) of pentafluorophenol and 11.6 g (56 mmol) of dicyclohexylcarbodiimide. Stirring is carried out for 10 hours at a temperature of 0° C., followed by filtration and shaking the filtrate at 0° C. with a 10% solution of potassium bicarbonate and water (100 ml of each) and then dried over anhydrous magnesium sulphate, filtered and evaporated. The resulting oily product containing pentafluorophenyl ester of tert.butoxycarbonylnitroarginine is dissolved in 300 ml of dimethylformamide, added with 9.25 g (80 mmol) of proline, N-methylmorpholine to pH=8 and water dropwise until proline is dissolved. The reaction mixture is kept for 2 hours at room temperature, then evaporated and the residue is dissolved in 100 ml of chloroform. The resulting solution is washed with 50 ml of a 10% solution of potassium bisulphate, 50 ml of water and then with 100 ml of a saturated solution of potassium bicarbonate. The bicarbonate extract is washed with 50 ml of ether and acidified with potassium bisulphate to pH=2. The resulting mixture is extracted with 100 ml of chloroform, the extract is washed with 50 ml of water and dried with anhydrous magnesium sulphate. The mass is then filtered, evaporated and the resulting oil is crystallized by rubbing with a mixture of ethylacetate and hexane (1:1). The yield of tert.butoxycarbonylnitroarginylproline (compound 6) is 10.3 g (46.1%) $\alpha_D^{20}$=−28.0° (c=1, dimethylformamide). $R_f$=0.14 (A), 0.50 (B), 0.78 (C), 0.67 (D), 0.84 (E).

From compound 6, in a manner similar to the synthesis of compound 2, there is prepared nitroarginylproline trifluoroacetate (compound 7). The yield is 99%, $\alpha_D^{20}$=−24.4° (c=1, dimethylformamide). $E_{his}$=0.65 (1 N acetic acid). $R_f$=0.08 (B), 0.20 (C), 0.22 (D), 0.40 (E).

10.0 g (18.5 mmol) of compound 5 and 7.78 g of compound 7 are dissolved in 100 ml of dimethylformamide and added with N-methylmorpholine to pH=8. The mixture is kept for 20 hours at room temperature, then it is evaporated and the residue is dissolved in 50 ml of chloroform, extracted with 50 ml of a 10% solution of potassium bisulphate (twice) and 50 ml of water. Upon evaporation of the chloroform solution, a crystalline residue is formed which is dispersed in ether, filtered and washed with ether on the filter. The yield of α-benzyloxycarbonyl, ε-/tert.butoxycarbonylnitroarginyl)-lysylnitroarginylproline (compound 8) is 11.7 g (96%).

$\alpha_D^{20} = -23.5°$ (c=1, dimethylformamide). $R_f = 0.02$ (A), 0.50 (B), 0.78 (C), 0.68 (D).

From compound 8, in a manner similar to the synthesis of compound 2 (except that instead of trifluoroacetic acid use is made of its mixture with methylene chloride in the volume ratio of (1:1) α-benzyloxycarbonyl, ε-(nitroarginyl)lysylnitroarginylproline trifluoroacetate (compound 9) is obtained. The yield is 96%. $\alpha_D^{20} = -12.0°$ (c=1, dimethylformamide). $E_{his} = 0.52$ (1 N acetic acid), $R_f = 0.16$ (B), 0.52 (C), 0.54 (D).

1.42 g (2.03 mmol) of compound 4 are dissolved in 50 ml of dimethylformamide and, upon cooling to −30° C., 0.66 ml (6.09 mmol) of a freshly-prepared 9.25 N solution of hydrogen chloride in dioxane in 5 ml of dimethylformamide and 0.31 ml (2.64 mmol) of tert-.butylnitrite in 3 ml of dimethylformamide are added thereto. The mixture is stirred for 30 minutes at −10° C. and then at −30° C. added thereto are a solution of 0.85 ml (6.09 mmol) of triethylamine in 10 ml of dimethylformamide and a solution of 1.81 g (2.03 mmole) of compound 9 and 0.28 ml (2.03 mmol) of triethylamine in 20 ml of dimethylformamide. The reaction mass is stirred at a temperature of 0° C. and a solution of 0.28 ml (2.03 mmol) of triethylamine in 10 ml of dimethylformamide is portionwise added at the rate of 2 ml every hour. Then the reaction mixture is maintained for 20 hours at 0° C., poured into 2 l of a 1% acetic acid, again maintained for 20 hours at 0° C. The resulting residue is filtered-off, washed with phosphorus pentoxide at 1 mm Hg. The yield of α-benzyloxycarbonyl, ε-/tert.butoxycarbonylphenylalanyl-O-benzylserylprolyl-phenylalanylnitroarginyl/lysylnitroarginylproline (compound 10) is 2.44 g (83%). $\alpha_D^{20} = -34.2°$ (c=1, dimethylformamide). $R_f = 0.06$ (A), 0.62 (B), 0.87 (C), 0.80 (D).

10.0 g (40 mmol) of benzyloxycarbonylproline are dissolved in 50 ml of dimethylformamide, added with 4.45 ml (40 mmol) of N-methylmorpholine and, at −15° C., a cooled solution of 5.30 ml (40 mmol) of isobutylchorocarbonate in 10 ml of dimethylformamide is dropwise introduced. Then the reaction mixture is stirred for additional 30 minutes at −15° C. and a cooled suspension of 10.6 g (50 mmol) of tert.butyl etherglycine-phosphite and 5.6 ml (50 mmol) of N-methylmorpholine is added thereto. The reaction mass is stirred for 30 minutes at a temperature of −15° C., then the reaction vessel is allowed to stay for 15 hours at −10° C. Then the reaction mass is evaporated and the residue is dissolved in a mixture of 100 ml of ethylacetate and 100 ml of water; the ethylacetate layer is washed with 10% solutions of potassium bicarbonate, potassium bisulphate and water (50 ml of each), dried with anhydrous magnesium sulphate, filtered and evaporated. The resulting oil is crystallized by treating with a mixture of ether with hexane (1:1). The yield of tert.butyl ester of benzyloxycarbonylprolylglycine (compound 11) is 9.2 g (63%). Melting point of the product is 71°–72° C. $\alpha_D^{20}$ is −49.0° (c=1, dimethylformamide); $R_f = 0.55$ (A), 0.64 (B), 0.68 (C).

5.0 g of compound 11 are hydrogenated in a solution of 50 ml of ethanol in the presence of palladium black for 5 hours. Then the catalyst is filtered-off, the filtrate is evaporated, the residue is dissolved in a mixture of dry ether with hexane (1:2) and again evaporated. Crystallization occurs thereby and after a complete evaporation a colourless crystalline compound is obtained. The yield of tert.butyl ester of prolylglycine (compound 12) is 2.8 g (89%). Melting point is 56°–57° C.

$\alpha_D^{20} = = -38.6°$ (c=1, dimethylformamide). $E_{His} = 0.83$ (1 N acetic acid).

2.44 g (1.68 mmol) of compound 10 are dissolved in 30 ml of dimethylformamide and added, at a temperature of 0° C., with 1.40 g (1.85 mmol) of a complex of dicyclohexylcarbodiimide with pentafluorophenol (1:3)/"complex F"/and 0.77 g of compound 12 (3.36 mmol). The reaction mixture is maintained for 20 hours at room temperature, evaporated and added with 50 ml of methylene chloride, filtered and the filtrate is evaporated, while the residue is rubbed with ether. The resulting product is charged into a column packed with silica gel (3×100 cm); passed through the column is first the chromatographic system A (1 liter), then B. The fractions absorbing at 280 nm are combined and again charged into a silica gel-packed column (3×250 cm) and eluted with system B. The fractions containing pure decapeptide (control by thin-layer chromatography) are combined, evaporated and rubbed with ether. The yield of tert.butyl ester of α-benzyloxycarbonyl, ε-/phenylalanyl-O-benzylserylprolylphenylalanylnitroarginyl/lysylnitroarginylprolylprolylglycine (compound 13) is 1.95 g (70%). $\alpha_D^{20} = -48.0°$ (c=1, dimethylformamide). $R_f = 0.8$ (A), 0.82 (B), 0.91 (C), 0.80 (D).

1.0 g (0.60 mmol) of compound 13 is dissolved in 10 ml of anhydrous methylene chloride and at a temperature of 0° C. 10 ml of a 8 N solution of dry hydrogen chloride in dioxane are added thereto. The reaction mixture is allowed to stay for 15 minutes at room temperature and evaporated at 20° C. The residue is rubbed with anhydrous ether. The yield of α-benzyloxycarbonyl, ε-/phenylalanyl-O-benzylserylprolylphenylalanyl-nitroarginyl/lysylnitroarginylprolylprolylglycine hydrochloride (compound 14) is 0.90 g (97%). $\alpha_D^{20} = -46.5°$ (c=1, dimethylformamide). $E_{His} = 0.43$ (5 N acetic acid), $R_f = 0.21$ (B), 0.76 (C), 0.58 (D).

0.33 g (0.214 mmol) of compound 14 and 0.30 ml (0.216 mmol) of triethylamine are dissolved in 800 ml of dimethylformamide (dimethylformamide is dried over barium oxide and distilled and then rectified over ninhydrin in an atmosphere of argon under a residual pressure of 1 mm Hg), cooled to a temperature of −6° C., added with 49.4 mg of N-hydroxysuccinimide (0.428 mmol) and under stirring in an atmosphere of argon a solution of 66.4 mg of dicyclohexylcarbodiimide in 100 ml of dimethylformamide is added thereto over 10 hours. The temperature of the mixture is thereby maintained at −6° C. Then the mixture is maintained for 20 hours at a temperature of −5° C. and for 36 hours at room temperature, after which it is evaporated and the residue is rubbed with ether and washed with water. The resulting compound is charged into a column with silica gel (2×100 cm), eluted with 0.5 ml of chromatographic system (A) and then with system B. The fractions containing the target cyclopeptide (the most chromatographically mobile component of a mixture of the peptide nature cyclization, absorbs at 280 nm) are combined and rubbed with ether. The yield of cyclo-/α-benzyloxycarbonyl, ε-(phenylalanyl-O-benzylserylprolyl-phenylalanylnitroarginyl)lysylnitroarginylprolyl-prolylglycyl (compound 15) is 25 mg (7.9%). $\alpha_D^{20} = -71.2°$ (c=0.5, methanol), $R_f = 0.03$ (A), 0.69 (B), 0.84 (C), 0.62 (D). 20 mg (0.0135 mmol) of compound 15 are dissolved in 1 ml of ethanol, added with 1 drop of acetic acid and 0.2 ml of water, followed by hydrogenation under atmospheric pressure for 70 hours in the presence of freshly prepared palladium black, filtered, evaporated and thrice lyophilized from water.

The yield of cyclo-/N$^\epsilon$-callidine/(compound I) is 17 mg (93%). The resulting compound is chromatographically and electrophoretically perfectly pure. Incubation with trypsin results in cleavage with the formation of callidine which, in turn, splits to lysine and bradikinin (electrophoresis and chromatography of the splitting products with markers) which proves the cyclic character of the product structure. $E_{His}=0.85$ (1 N acetic acid $R_f=0.60$ (methanol-water-ammoniumacetate 9.5 ml:0.5 ml:0.15 g); silanized plate "Merck".

EXAMPLE 2

6.4 g (16.6 mmol) of p-nitrophenyl ester of tert.butoxycarbonylphenylalanine, 1.13 g (15 mmol) of glycine and 1.67 ml (15 mmol) of glycine and 1.67 ml (15 mmol) of N-methylmorpholine are dissolved in a mixture of 200 ml of dimethylformamide and 20 ml of water. The resulting solution is allowed to stay for 20 hours at room temperature, after which it is evaporated and the residual oil is dissolved in a mixture of 80 ml of a 10% aqueous solution of potassium bicarbonate and 50 ml of ethylacetate. The ethylacetate layer is separated, while the aqueous layer is extracted with ether (50 ml) and neutralized with an excess of a 10% aqueous solution of potassium bisulphate (to pH 2). The resulting solution is extracted with ethylacetate (2×50 ml), the extract is washed with water (50 ml- dried over anhydrous magnesium sulphate, filtered and evaporated to dryness. A colourless crystalline substance is obtained. The yield of tert.butoxycarbonylphenylalanylglycine (compound 16) is 4.0 g (82.7%). For analytical purposes the product is crystallized from ethylacetate. Melting point is 165° C. with decomposition. $\alpha_D^{20}=-9.0°$ (c=1, dimethylformamide $R_f=0.85$ (A), 0.90 (B), 0.88 (C).

2.80 g (8.7 mmol) of compound 16 are dissolved in 50 ml of dry dimethylformamide, added with 1.84 g (10 mmol) of pentafluorophenol and cooled to $-20°$ C., after which 1.90 g (9.2 mmol) of dicyclohexylcarbodiimide are added; the mixture is shaken until dissolution of the latter and maintained for 30 minutes at a temperature of 0° C. Then there are added 4.15 g (8.7 mmol) of prolylphenylalanine hydrobromide p-nitrobenzyl ether and N-methylmorpholine to pH=8. The mixture is maintained for 3 hours at room temperature, evaporated and the residue is added with 100 ml of methylene chloride, filtered and the filtrate is extracted with 10% solutions of potassium bicarbonate, potassium bisulphate and water (100 ml each). The reaction mass is dried over anhydrous magnesium sulphate, filtered and the filtrate is evaporated. An oil is formed which is crystallized by rubbing with anhydrous ether. The yield of p-nitrobeznyl ester of tert.butoxycarbonylphenylalanylglycyl-prolylphenylalanine (compound 17) is 5.4 g (88.4%). Melting point is 125°-155° C. $\alpha_D^{20}=-45.6°$ (c=1, dimethylformamide), $R_f=0.88$ (A), 0.91 (B), 0.91 (D).

3.0 g (4.26 mmol) of compound 17 and 1.0 ml of hydrazine hydrate are heated for 1 hour in 30 ml of ethanol at 70° C., filtered and the filtrate is added with 50 ml and maintained for 20 hours at a temperature of $-10°$ C., filtered-off and crystals on the filter are washed with 30 ml of a 50% aqueous ethanol, then with water to neutral reaction of the filtrate. The product is dried in a desiccator over phosphorus pentoxide. The yield of tert.butoxycarbonylphenylalanylpropylylphenylalanine hydrazide (compound 18) is 2.30 g (92.8%), melting point 140°-160° C. $\alpha_D^{20}=-59.8°$ (c=1, dimethylformamide). $R_f=0.93$ (A), 0.92 (B), 0.91 (D).

10.0 g (14.2 mmol) of compound 5 are dissolved in 100 ml of dimethylformamide, added with 2.46 g (21.4 mmol) of a finely divided proline and 1.66 ml (14.9 mmol) of N-methylmorpholine and stirred, using a magnetic stirrer, for 20 hours. Then the reaction mixture is evaporated, the residue is dissolved in a mixture of 100 ml of ethylacetate and 100 ml of a 10% solution of potassium bisulphate, the aqueous layer is separated and the ethylacetate layer is extracted with a 10% solution of potassium bisulphate and then with a 10% solution of potassium bicarbonate (100 ml each). The aqueo-bicarbonate layer is separated, neutralized with an excess of a 10% solution of potassium bisulphate to pH=2 and extracted with ethylacetate (2×100 ml). The extract is dried with anhydrous magnesium sulphate, filtered and evaporated to give a colourless amorphous substance. The yield of α-benzyloxycarbonyl, $\epsilon$-(tert.butoxycarbonylnitroarginyl))lysylproline (compound 19) is 7.9 g (82%); $\alpha_D^{20}=-23.1°$ (c=1, dimethylformamide). $R_f=0.54$ (A) 0.81 (D). From compound 19 in a manner similar to the synthesis of compound 2 there is prepared α-benzyloxycarbonyl, $\epsilon$-(nitroarginyl))lysylproline (compound 20). The yield is 98%. $E_{His}=49$ (5 N acetic acid), $\alpha_D^{20}=-11.1°$ (c=1, dimethylformamide). $R_f=0.57$ (C), 0.70 (E).

2.1 g (3.62 mmol) of compound 18 are dissolved in 50 ml of dimethylformamide, cooled to a temperature of $-30°$ C. and a cooled ($-70°$ C.) mixture of 3.5 ml (15.7 mmol) of 4.5 N solution of dry hydrogen chloride in tetrahydrofuran and 20 ml of ethylacetate is added thereto under stirring. Then at a temperature of $-30°$ C. a cooled solution of 0.45 ml (3.87 mmol) of tert.butylnitrite in 10 ml of ethylacetate is added dropwise; the mixture is maintained at a temperature of $-25°$ C. for 30 minutes and then added with 1.76 ml (15.8 mmol) of N-methylmorpholine; afterwards, a solution of 2.68 g of compound 20 (3.87 mmol) and 0.44 ml of N-methylmorpholine in 50 ml of dimethylformamide is introduced. The reaction mixture is kept for three days at a temperature of $-10°$ C., evaporated and the residue is dissolved in a mixture of 100 ml of methylene chloride and 100 ml of water. The layer of methylene chloride is separated, successively washed with 10% solutions of potassium bicarbonate, potassium bisulphate and water (100 ml each), dried over anhydrous magnesium sulphate, filtered and evaporated to give an oil which is crystallized upon rubbing with a mixture of ether with ethylacetate (I:I). The yield of α-benzyloxycarbonyl, $\epsilon$-(tert.-butoxycarbonylphenylalanylglycylprolylphenylalanylnitroarginyl))lysylproline (compound 21) is 3.50 g (85.8%), Melting point is 140°-177° C.; $\alpha_D^{20}=-44.1°$ (c=1, dimethylformamide). $R_f=0.53$ (A), 0.37 (B), 0.87 (D).

2.70 g (2.40 mmol) of compound 21 are dissolved in 40 ml of dimethylformamide, cooled to 0° C. and added with 2.19 g (2.89 mmol) of "complex F" and 1.1 g (4.8 mmol) of compound 12. Then the reaction mixture is maintained for 20 hours at room temperature, evaporated, the residue is dissolved in 50 ml of methylene chloride, filtered, the filtrate is washed with 50 ml of a 10% solution of potassium bisulphate and 50 ml of water. The product is dried over anhydrous magnesium sulphate, filtered and evaporated. The precipitate is twice dissolved in a minimal volume of methylene chloride and precipitated with ether. The yield of tert.butyl ester of α-benzyloxycarbonyl-$\epsilon$-(tert.butoxycarbonyl-phenylalanylglycylprolylphenylalanylnitroarginyl)-lysylprolylprolylglycine (compound 22) is 2.8 g (87.2%), melting temperature 150°–193° C. with decomposition, $a_D^{20} = -60.3°$ C. (c=1, dimethylformamide). $R_f = 0.57$ (A), 0.80 (B), 0.60 (D).

1.8 g (1.35 mmol) of compound 22 at a temperature of 0° C. are dissolved in 20 ml of a mixture of trifluoroacetic acid with methylene chloride (1:1), maintained for 20 minutes at room temperature and evaporated at 0° C. The residue is crystallized by rubbing with 50 ml of dry ether, dissolved in 10 ml of anhydrous dimethylformamide, added with 0.33 ml (1.5 mmol) of a 4.5 N solution of anhydrous hydrogen chloride in tetrahydrofuran and precipitated with 100 ml of ether. The yield of α-benzyloxycarbonyl-ε-(phenylalanylglycylprolyl-phenylalanylnitroarginyl)lysylprolylprolylglycine hydrochloride is 1.55 g (95%) (compound 23). $a_D^{20} = -77.8°$, melting temperature 140° to 192° C. $R_f = 0.73$ (C), 0.74 (E).

1.1 g (0.91 mmol) of compound 23 is dissolved in 2 ml of dimethylformamide (dried over barium oxide and distilled over ninhydrin directly before use) and, while stirring in a atmosphere of dry argon at 0° C., added with 1.5 g (1.98 mmol) of "complex F". Then at room temperature for 6 hours a solution of 0.19 ml (1.33 mmol) of triethylamine in 300 ml of dimethylformamide is added. The resulting mixture is kept at room temperature for two days and evaporated. The residue is crystallized by rubbing with anhydrous ether, filtered, the residue on the filter is washed with ether and then with water. The resulting product is investigated using thin-layer chromatography techniques in system B. It is suggested that the compound with $R_f = 0.4$ is the required cyclopeptide (one of the main cyclization products, chromatographically mobile; detected by visualization in UV-light and benzidine reagent). The cyclization mixture is preliminary purified on a column with silica gel (2×100 cm) using the system chloroform-ethanol-n.butanol-ethylacetate (10:6:4:3) as an eluent. The fractions containing the target cyclopeptide are again purified on a column with silica gel (3×250 cm) using system B as the eluent. The fractions containing the pure cyclopeptide are combined, evaporated and the residue is rubbed with ether. The yield of cyclo/α-benzyloxycarbonyl, ε-(phenylalanylglycylprolyl-phenylalanylnitroarginyl)lysylprolylprolylglycyl/-(compound 24) is 102 mg (9.7%). Melting point is 163°–165° C. Molecular weight: found: 1,024 (determined cryoscopically using urea melt); calculated by the formula: 1,163.31. $a_D^{20} = 64.1°$ (c=0.5, dimethylformamide). $R_f = 0.37$ (A), 0.43 (B), 0.89 (C), 0.37 (D), 0.96(E).

26 mg (0.0223 mmol) of compound 24 are dissolved in 0.5 ml of glacial acetic acid and then added with 0.2 ml of a freshly prepared saturated solution of dry hydrogen bromide in acetic acid. The mixture is maintained for one hour at room temperature and then added with 5 ml of anhydrous ether. The resulting residue is dispersed 10 times in 5 ml of an anhydrous ether and decanted, followed by keeping in a desiccator at 1 mm Hg over potassium hydroxide. The yield of cyclo-/(ε-phenylalanylglycylprolylphenylalanylnitroarginyl)-lysylprolylglycyl/hydrobromide is 23.4 mg (94.7%). $E_{His} = 0.38$ (5 N acetic acid). $a_D^{20} = -48.0°$ (c=0.5, dimethylformamide).

20 mg (0.018 mmol) of compound 25 are dissolved in 0.5 ml of dimethylformamide, added with 26.7 mg (0.036 mmol) of pentafluorophenyl ester of tribenzyloxycarbonylarginine and a solution of N-methylmorpholine in dimethylformamide to pH=8. The reaction mixture is kept for one hour at room temperature, evaporated and the residue is rubbed with 3 ml of anhydrous ethylacetate; the resulting precipitate is thrice dispersed in anhydrous ethylacetate and decanted. Then the residue is dried by means of compressed air jet and 3 times dispersed in 3 ml of water and decanted. Drying is effected over potassium hydroxide and phosphorus pentoxide under a residual pressure of 1 mm Hg. The yield of $N^\alpha$-tribenzyloxycarbonyl-cyclo/ε-(phenylalanylglycylprolylphenylalanylnitroarginyl)-lysylprolylglycyl/(compound 26) is 26.0 mg (91%). $R_f = 0.67$ (B), $a_D^{20} = -61.2$ (c=0.5, acetic acid).

23 mg (0.014 mmol) of compound 26 are hydrogenated under atmospheric pressure in the presence of palladium black in a mixture with 0.4 ml of acetic acid, 0.2 ml of methanol and 0.04 ml of water over a period of 20 hours, followed by evaporation and lyophilization from water to obtain a loose powder. The product is electrophoretically and chromatographically uniform. The yield of $N^\alpha$-arginylcyclo/($N^\epsilon$-1-lysine, 6-glycine)-bradikinin/(compound 2) is 17.7 mg (96%); $E_{His} = 0.80$ (1 N Acetic acid); $a_D^{20} = -0.62$ (c=0.5, H$_2$O).

EXAMPLE 3

1.03 g (22.3 mmol) of pentafluorophenyl ester of tert.butoxycarbonyl-o-benzylserine and 6.7 g (23.4 mmol) of p-nitrobenzyl ester of proline hydrochloride are dissolved in 200 ml of dimethylformamide and triethylamine is added to the pH=8. The reaction mixture is stirred for 2 hours at room temperature, evaporated, the residue is dissolved in a mixture of 100 ml of ether and 100 ml of water. The organic layer is separated and extracted with 100 ml of a 10% solution of potassium bicarbonate and then with 100 ml of a 10% solution of potassium bisulphate, dried over anhydrous magnesium sulphate, filtered and evaporated. An oil is obtained which contains p-nitrobenzyl ester of tert.butoxycarbonyl-o-benzylserylproline (compound 27); $R_f = 0.95$ (A), 0.77 (B), 0.95 (C), 0.76 (D) and pentafluorophenol. It is dissolved in trifluoroacetic acid, maintained for 20 minutes at room temperature and then evaporated. The residue containing p-nitrobenzyl ester of O-benzylseryl-proline trofluoroacetate (compound 28) is neutralized with triethylamine to the pH=8, added with 10 g (23.2 mmol) of pentafluorophenyl ester of tert.butoxycarbonylphenylalanine. The mixture is kept for one hour at room temperature, then added with 1 ml of β-dimethylaminoethylamine. 10 minutes later, the mixture is neutralized with acetic acid to pH=6, evaporated and the residue is dissolved in a mixture of 100 ml of ether and 100 ml of water; the ethereal layer is separated, washed with 100 ml of a 10% potassium bisulphate, then with 100 ml of water. There are added 50 ml of benzene, the mixture is evaporated and the resulting dark-brown oil is chromatographically purified (700 g of silica gel, elution first with a mixture of heptane-ethylacetate/5:1/, then with chromatographic system A). After evaporation of the eluate a lightbrown oil is obtained. The yield of p-nitrobenzyl ester of tert.butoxycarbonylphenylalanyl-o-benzylserylproline (compound 29) is 9.7 g (64.5%). For the analytical purposes a small portion thereof is crystallized by rubbing with hexane. $a_D^{23} = 29.1°$ (c=1, dimethylformamide); $R_f = 0.94$ (A), 0.77 (B), 0.96 (C), 0.81 (D).

From compound 29 in a manner similar to the synthesis of compound 2 described hereinbefore there is obtained p-nitrobenzyl ester of phenylalanyl-o-benzylserylproline trifluoroacetate (compound 30) comprising an oily product, the yield 8.9 g (97%).

For analytical purposes a small portion of the oil is crystallized by rubbing with hexane. $\alpha_D^{23}=16.3°$ (c=1, dimethylformamide); $E_{His}=0.61$ (1 N acetic acid); $R_f=0.12$ (A), 0.66 (B), 0.88 (C), 0.62 (D).

From compound 30 in a manner similar to the synthesis of compound 29, using pentafluorophenyl ester of tert.butoxycarbonylglycine, there is obtained a mixture consisting of p-nitrobenzyl ester of tert.butoxycarbonylglycylphenylalanyl-o-benzylserylproline (compound 31)/$R_f=-0.71$ (A, 0.76 (B), 0.95 (C), 0.80 (D)/and pentafluorophenol which is treated with trifluoroacetic acid as in the preparation of compound 28 to give an oil containing p-nitrobenzyl ester of glycylphenylalanyl-o-benzylserylproline trifluoroacetate (compound 32); $E_{His}=0.58$ (1 N acetic acid); $R_f=0.02$ (A), 0.2 (B), 0.67 (C), 0.62 (D). The oil containing compound 32 is neutralized and employed for the reaction with pentafluorophenyl ester of tert.butoxycarbonylproline in a manner similar to that used in the preparation of compound 29. The resulting oil is chromatographically purified (700 g of silica gel, first eluted with chloroform, then with a mixture of chromatographic system A with isopropanol/4:1/). After evaporation of the eluate a light-brown oil is obtained which is crystallized by rubbing with a mixture of ether and hexane (1:1). The yield of p-nitrobenzyl ester of tert.butoxycarbonylprolylglycylphenylalanyl-o-benzylserylproline (compound 33) is 62%. $\alpha_D^{29}=-43.0°$ (c=1, dimethylformamide), $R_f=0.58$ (A), 0.72 (B), 0.94 (C), 0.78 (D).

2.5 g (3.0 mmol) of the compound 33 are dissolved in 20 ml of methylene chloride, then added with 4 ml of trifluoroacetic acid. The reaction mixture is maintained for 2 hours at room temperature, evaporated and the residue is crystallized by rubbing with anhydrous ether. The yield of p-nitrobenzyl ester of prolylglycylphenylalanyl-o-benzylserylproline trifuoroacetate (compound 34) is 2.47 g (98%). $\alpha_D^{29}=-27.8°$ (c=1, dimethylformamide), $E_{His}=0.57$ (1 N acetic acid); $R_f=0$ (A), 0.13 (B), 0.81 (C), 0.26 (D). 1.36 g (3.27 mmol) of compound 6 0.60 g (3.27 mmol) of pentafluorophenol and 0.67 g (3.27 mmol) of dicyclohexylcarbodiimide are dissolved at a temperature of 0° C. in 50 ml of anhydrous methylene chloride, maintained for one hour and filtered. In the filtrate there are dissolved 2.36 g (2.8 mmol) of compound 34 and thriethylamine is added thereto to a pH value of 8. The mixture is kept for 20 hours at room temperature. The mixture is extracted with 50 ml of a 10% potassium bicarbonate, then with 50 ml of a 10% potassium bisulphate and 50 ml of water; evaporated and the residue is chromatographically purified (200 g of silica gel, eluent: chromatographic system A and isopropanol/4:1/). The residue after evaporation is crystallized by rubbing with ether. The yield of p-nitrobenzyl ester of tert.butoxycarbonylnitroarginylprolylprolylglycylphenylalanyl-o-benzylserylproline (compound 35) is 1.9 g (60%); $\alpha_D^{29}=-50.0°$ (c=1, dimethylformamide); $R_f=0.08$ (A), 0.61 (B), 0.96 (C); 0.56 (D).

1.45 g (1.29 mmol) of compound 35 is dissolved in 18 ml of acetone, added with 7 ml of water, 1 mg of thymolphthalein and, under stirring, 1.3 ml of a 1 N sodium hydroxide (portion-wise by portions of 0.3 ml) for 7 hours. The next portion of the alkali is added after disappearance of blue colour. Neutralization is then effected using a 10% solution of potassium bisulphate and evaporation is conducted until acetone odour disappears. Then there are added 30 ml of methylene chloride and the organic layer is washed with 30 ml of a 1% solution of potassium bisulphate and water (thrice by portions of 30 ml), evaporated, the residue is crystallized by rubbing with anhydrous ether. The yield of tert.butoxycarbonylnitroarginylprolylprolylglycylphenylalanyl-o-benzylserylproline (compound 36) is 1.1 g (86%); $\alpha_D^{29}=-56.5°$ (c=1, dimethylformamide); $R_f=0.04$ (A), 0.56 (B), 0.90 (C), 0.54 (D).

5 g (13.4 mmol) of tert.butoxycarbonylnitroarginine are converted to pentafluorophenyl ester (following the procedure of the above-described synthesis of compound 6). The oil containing pentafluorophenyl ester of tert.butoxycarbonylnitroarginine is dissolved in 75 ml of dimethylformamide, added with 4.3 g (20 mmol) of ω-aminododecane acid, N-methylmorpholine to a pH value of 8 and 20 ml of water, vigorously stirred at room temperature for 20 hours, filtered; the filtrate is evaporated, the residue is chromatographically purified (1 kg of silica gel, first elution with chromatographic system A, then with a mixture of chromatographic system A and isopropanol/4:1/). The residue after evaporation of the eluate is crystallized by rubbing with hexane. The yield of tert.butoxycarbonylnitroarginyl-ωaminododecane acid (compound 37) is 1.5 g (22%); $\alpha_D^{23}=-4.1°$ (c=1, dimethylformamide); $R_f=0.19$ (A), 0.70 (B), 0.87 (C), 0.75 (D).

From compound 37, following the procedure of the synthesis of compound 2 described hereinbefore, there is obtained nitroarginyl-ω-aminododecane acid trifluoroacetate (compound 38). The yield is 96%; $E_{his}=0.58$ (1 N acetic acid); $R_f=0$ (A), 0.33 (B), 0.48 (C), 0.55 (D).

1.3 g (2.45 mmol) of compound 38 are dissolved in 30 ml of dimethylformamide, added with N-methylmorpholine to a pH value of 8, and then with 2.0 g (4.6 mmol) of pentafluorophenyl ester of tert.butoxycarbonylphenylalanine. The mixture is maintained for one hour at room temperature, evaporated, the residue is dissolved in 50 ml of methylene chloride and washed with 50 ml of a 10% potassium bisulphite and 50 ml of water (twice). The product is evaporated, the residue is chromatographically purified (200 g of silica gel, elution with chromatographic system A). The residue after evaporation of the eluate fraction is crystallized by rubbing with hexane. The yield of tert.butoxycarbonylphenylalanylnitroarginyl-ω-aminododecane acid (compound 39) is 0.5 g (31%); $\alpha_D^{29}=-13.5°$ (c=0.2, dimethylformamide); $R_f=0.19$ (A), 0.76 (B), 0.91 (C), 0.80 (D).

0.45 g (0.68 mmol) of compound 39 is dissolved in 10 ml of glacial acetic acid and added with 1 ml of a saturated solution of anhydrous hydrogen chloride in dioxane, maintained for 30 minutes at room temperature and evaporated. The residue is crystallized by rubbing with anhydrous ether, dried in a desiccator over potassium hydroxide. The yield of phenylalanylnitroarginyl-ω-amino-dodecane acid hydrochloride (compound 40) is 0.4 g (98%); $\alpha_D^{29}=+3.8°$ (c=1, dimethylformamide); $E_{His}=0.44$ (1 N acetic acid); $R_f=0$ (A), 0.79 (C), 0.50 (D).

0.76 g (0.77 mmol) of compound 36 and 0.53 g (0.70 mmol) of "Complex F" are dissolved in 20 ml of anhydrous dimethylformamide, maintained for 12 hours at room temperature, then added with 0.4 g (0.67 mmol) of compound 40 and diisopropylethylamine to a pH value of 8. The mixture is maintained for 20 hours at room temperature, then evaporated and the residue is rubbed with anhydrous ether. Chromatographic purification is effected using 1 kg of silica gel and chromatographic system B as the eluent at a 5-time circulation. The residue after evaporation of the eluate fraction is crystallized by rubbing with anhydrous ether. The yield of tert.butoxycarbonylnitroarginylprolylprolylglycylphenylalanyl-o-benzylserylprolylphenylalanylnitroarginyl-ω-aminododecane acid (compound 41) is 0.56 g (54%). $\alpha_D^{29}=47.5°$ (c=1, dimethylformamide); $R_f=0$ (a), 0.89 (C), 0.64 (D).

100 mg (0.065 mmol) of compound 41 and 67.3 mg (0.089 mmol) of "complex F" are dissolved in 20 ml of anhydrous methylene chloride, maintained for 20 hours at room temperature, evaporated and the residue is rubbed with anhydrous ether. The yield of pentafluorophenyl ester of tert.butoxycarbonylnitroarginylprolylprolylglycylphenylalanyl-o-benzylserylprolylphenylalanylnitroarginyl-ω-aminododecane acid (compound 42) is 105 mg (95%).

100 mg (0.059 mmol) of compound 42 are dissolved in 2 ml of anhydrous methylene chloride, added with 0.1 ml of saturated solution of anhydrous hydrogen chloride in dioxane. The reaction mixture is maintained for 30 minutes at room temperature and then added with 20 ml of anhydrous ether. The resulting residue is filtered, washed with anhydrous ether, kept in a vacuum desiccator over potassium hydroxide. The yield of pentafluorophenyl ester of nitroarginylprolylprolylglycylphenylalanyl-o-benzylserylprolylphenylalanylnitroarginyl-ω-aminododecane acid hydrochloride (compound 43) is 92 mg (95%).

To a solution of 0.11 ml (0.64 mmol) of diisopropylethylamine in 200 ml of dimethylformamide under vigorous stirring there is added a solution of 90 mg (0.055 mmol) of compound 43 in 10 ml of dimethylformamide, maintained for 2 days at room temperature and evaporated. The residue is crystallized by rubbing with anhydrous ether, then chromatographed (200 g of silica gel, eluent: chromatographic system A-isopropanol/4:1/, then chromatographic system B). The eluate fraction containing the cyclopeptide is evaporated and the residue is again chromatographed (100 g of silica gel, eluent-alcohol). After evaporation of the eluate fraction the residue is crystallized by rubbing with anhydrous ether, then dried and intermixed with 3 ml of water, decanted and again washed with water. Thereafter the product is dried in a vacuum desiccator over phosphorus pentoxide. The yield of cyclo-/nitroarginylprolylprolylglycylphenylalanyl-o-benzylserylprolylphenylalanylnitroarginyl-ω-aminododecanoyl (compound 44) is 20 mg (26%); $\alpha_D^{24}=-46.2°$ (c=1, methanol). $R_f=0$ (A), 0.59 (B), 0.88 (C).

20 mg (0.014 mmol) of compound 44 are dissolved in 2 ml of methanol, added with 1 drop of acetic acid and hydrogenated for 24 hours in the presence of palladium black, then filtered, evaporated and the residue is dissolved in 2 ml of water, filtered and lyophilized to give a white powder. The yield of cyclo-/(ω-aminododecanoyl) bradikinin/diacetate is 13 mg (68%). $\alpha_D^{20}=63.2°$ (c=0.5, water); $E_{His}=0.67$ (1 N acetic acid); $R_f=0.32$ (D).

What is claimed is:

1. Cyclic analogues of callidine of the formula:

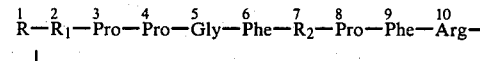

wherein Pro is a moiety of L-proline, Gly - that of glycine, Phe is a moiety of L-phenylalanine; Arg - that of L-arginine; R is a residue of α- or ω-lysine or arginine; $R_1$ is a residue or α- or ω-lysine or arginine; $R_2$ is L-serine, and the carbonyl group of arginine is connected with either R or $R_1$ by means of a covalent peptide bond using the ω-amino group of the R or $R_1$ located at 1 or 2 position of callidine.

2. Cyclo-/$N^\epsilon$-callidine/of claim 1 of the formula:

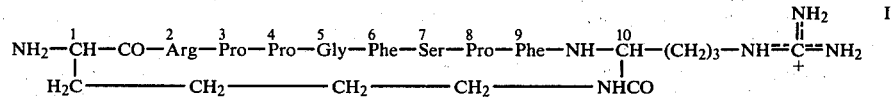

3. $N^\alpha$-arginyl-cyclo-/($N^\epsilon$-1-lysine, 6-glycine)-bradikinin/of claim 1 of the formula:

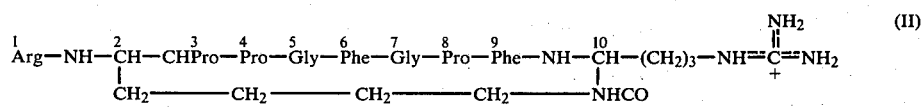

4. Cyclo-/(ω-aminododecanoyl)bradikinin/of claim 1 of the formula:

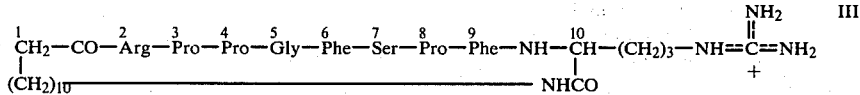

5. Cyclo-/(ω-aminododecanoyl-ω-aminododecanoyl)bradikinin/of claim 1 of the formula:

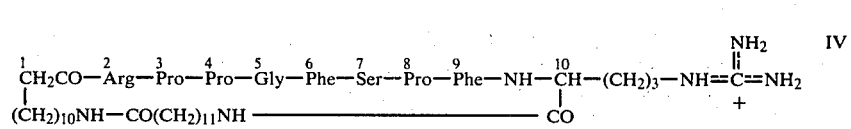

* * * * *